United States Patent [19]

Palit et al.

[11] Patent Number: 5,945,455
[45] Date of Patent: Aug. 31, 1999

[54] AMINE AND AMIDINE CONTAINING COMPOUNDS AS WEIGHT REDUCING AGENTS

[75] Inventors: Piali Palit, Liverpool; Brian Laurence Furman, Glasgow; Alexander Irvine Gray, Glasgow; Roger David Waigh, Glasgow, all of United Kingdom

[73] Assignee: University of Strathclyde, Glasgow, United Kingdom

[21] Appl. No.: 08/952,538

[22] PCT Filed: May 17, 1996

[86] PCT No.: PCT/GB96/01191

§ 371 Date: Apr. 15, 1998

§ 102(e) Date: Apr. 15, 1998

[87] PCT Pub. No.: WO96/36325

PCT Pub. Date: Nov. 21, 1996

[30] Foreign Application Priority Data

May 19, 1995 [GB] United Kingdom .................... 9511757

[51] Int. Cl.⁶ ..................................................... A61K 31/13
[52] U.S. Cl. ............................................ 514/634; 514/910
[58] Field of Search ..................................... 514/634, 910

[56] References Cited

FOREIGN PATENT DOCUMENTS 189 162   7/1988   Hungary .
94/03714  3/1993   WIPO .

OTHER PUBLICATIONS

CA103:213827, Balogh, Abstract for HU 35160, 1985.

"The Merck Index, 11th Edition" 1989, Merck & Co., Inc., Monograph 616: Amphetamine, p. 92.

Hoppe–Seyler's Z. Physiol. Chem., vol. 353, No. 4, Apr. 1972, pp. 535–539, G. Weitzel et al: "Antilipolytische Wirksamkeit von Arginylverbindungen".

Hoppe–Seyler's Z. Physiol. Chem., vol. 352, No. 12, Dec. 1971, pp. 1617–1630, G. Weitzel et al: "Indulinähnliche Aktivität von Arginylverbinsungen in vitro".

Eur. J. Clin. Invest. vol. 3, No. 3, 1973, p. 208, K.G.M.M. Alberti et al: "Mechanism of Action of the Monoguanidine Hypoglycaemic Agents, Galegine and Agmatine".

Fitoterapia, vol. 65, No. 5, 1994, pp. 423–426, K. Pundarikakshudu et al: "Studies on the hypoglycaemic activity of Galega officinalis (goat's rue)".

Primary Examiner—Rebecca Cook
Attorney, Agent, or Firm—Alston & Bird LLP

[57] ABSTRACT

Use of amine and amidine containing compounds of formula (I) such as galegine and related substituted amine and amidine containing compounds as agents for reducing weight in mammals, pharmaceutical formulations containing a compound of formula (I) and methods of attaining weight reduction in mammals.

2 Claims, 6 Drawing Sheets

AMINE AND AMIDINE CONTAINING COMPOUNDS AS WEIGHT REDUCING AGENTS

This is a 371 of PCT/GB96/01191 filed May 17, 1996.

FIELD OF THE INVENTION

The present invention relates to the use of amine and amidine containing compounds such as galegine ((3-methyl-2-butenyl) guanidine) and related substituted amine and amidine containing compounds, as agents for reducing weight in mammals.

BACKGROUND OF THE INVENTION

Being obese or over-weight is a common problem. Aggravating factors may be depression or other psychosocial problems. Patients receiving drug treatment are also often predisposed to weight gain.

Obesity can be controlled to some extent by strict dieting, however, dieting is seldom successful in the long term as the subject may find it difficult to stick to a dieting regime.

Obesity can aggravate certain medical conditions, and is a risk factor for heart disease.

Galegine is an example of an amidine group containing compound which is known to have hypoglycaemic effect. It has now been unexpectedly found that When galegine is administered to a mammal, a weight reduction effect is observed.

SUMMARY OF THE INVENTION

One aspect of the present invention provides the use of a compound of formula (I):

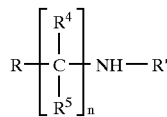

(I)

wherein

R is selected from the group phenyl and

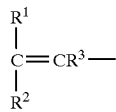

where

R$^1$, R$^2$ and R$^3$ are independently selected from the group H, C$_{1-6}$ alkyl, C$_{2-6}$ alkenyl, and C$_{2-6}$, alkynyl;

R$^4$ and R$^5$ are independently selected from H, C$_{1-6}$ alkyl, C$_{2-6}$ alkenyl, and C$_{2-6}$alkynyl;

R' is

wherein R$^6$ is selected from the group H, NH$_2$ and C$_{1-6}$ alkyl; n is a whole integer from 0 to 6; and physiologically acceptable salts thereof in the manufacture of a composition for weight reduction, with the proviso that when R' is

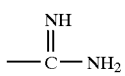

and n=0, R is not phenyl and when R' is

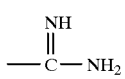

and n is 1, 2, 3 or 4 and R$^4$ and R$^5$ are both H, R is not phenyl.

Preferably R$^1$, R$^2$, R$^3$, R$^4$ and R$^5$ are independently selected from the group H, C$_{1-2}$ alkyl, C$_{2-3}$, alkenyl and C$_{2-3}$ alkynyl;

R' is

wherein R$^6$ is selected from the group NH$_2$, H and C$_{1-2}$ alkyl; and n is a whole integer from 0 to 2; and physiologically acceptable salts thereof.

In a preferment, the invention provides the use of a compound of formula (II) in the manufacture of a composition for weight reduction,

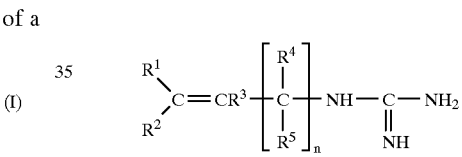

(II)

wherein

R$^1$, R$^2$, R$^3$, R$^4$ and R$^5$ independently selected from hydrogen, C$_{1-6}$ alkyl, C$_{2-6}$ alkenyl, C$_{2-6}$ alkynyl and NH$_2$; and n is from 0 to 6; and physiologically acceptable salts thereof.

Compounds of formula (I) or formula (II) hereafter are referred to as "weight reducing agent". Another aspect of the present invention provides a method of reducing weight in a subject which comprises administering to a subject an effective non-toxic amount of a weight reducing agent of formula (I). In a preferment, the effective non-toxic amount of weight reducing agent is of formula (II).

A further aspect of the present invention is the suppression of appetite i.e. food intake in a subject generically predisposed to obesity. Thus it has been found that food intake is suppressed in genetically obese subjects, but does not show a longterm suppression in a normal subject.

BRIEF DESCRIPTION OF THE DRAWINGS

The weight reduction effect demonstrated by weight reducing agents of the present invention is unexpected since reduction in glucose levels caused by known hypoglycaemic compounds does not necessarily lead to weight reduction and may in fact lead to increase in weight.

Preferably, R$^1$ and R$^2$ of formula (II) are both C$_{1-6}$ alkyl, or C$_{2-6}$ alkenyl or C$_{2-6}$ alkynyl, particularly methyl or ethyl; ethenyl or methenyl; methynyl or ethynyl; or mixtures thereof. Generally, $R^3$ of formula (II) is hydrogen or $C_{1-6}$ alkyl. $R^4$ and $R^5$ of formula (II) are preferably hydrogen or $C_{1-6}$ alkyl; and n is usually 1 or 2.

Figure 1:
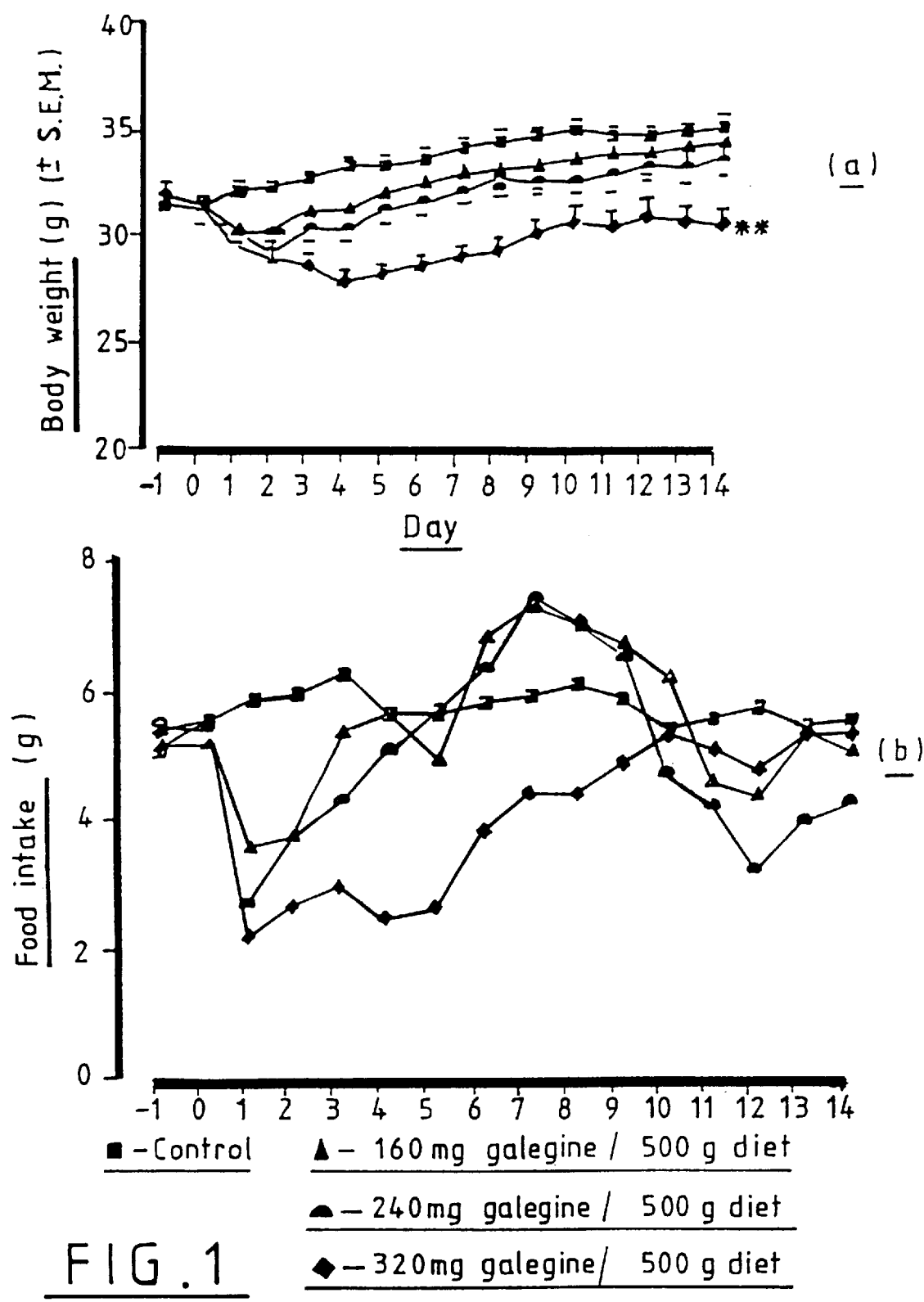

A particularly preferred compound is galegine, (3-methyl-2-butenyl) guanidine, where $R^1$ and $R^2$ are both methyl, $R^3$, $R^4$ and $R^5$ are hydrogen, and n is unity.

Also included as An aspect of the invention are novel compounds according to formula (I) and/or (II) such as γ,γ-dimethylallyl amidine and physiologically acceptable salts thereof, such as acid addition salts and the like.

Galegine can be isolated from the plant *Galega officinalis* (e.g. Tanret, *Compt Rend* 158 1182, (1914); Markovic & Dittertova *Chem Zvesti* 9 576 (1955)). Extracts from the plant *Galega officinalis* can be extracted using solvent systems comprising polar organic solvent systems or solvent systems comprising a mixture of at least one polar organic solvent in admixture with water. Suitable polar organic solvents include supercritical $CO_2$, alcohols such as methanol and ethanol, and physiologically acceptable glycols such as propylene glycol. It is preferred if the polar organic solvent is one which is pharmaceutically acceptable to the mammal in the sense that any deleterious side effects which may occur in the mammal are transient in nature and do not give rise to a disease state. A preferred solvent system which has been found to give rise to extracts of *galega officinalis* having a weight reducing effect is the solvent system 50% ethanol: 50% $H_2O$. Generally, extracts of *Galega officinalis* in solvent systems should be physiologically acceptable to the recipient mammal and substantially non-toxic thereto. Extracts of *Galega officinalis* can be prepared as follows. *Galega officinalis* plant material (e.g. leaves, stems, shoots, flower parts) can be dried, then pulverised to form a powder. A desired amount of the powdered plant material can then be extracted to exhaustion using conventional solvent extraction technology, for example, first with ethyl acetate followed by polar organic solvent (e.g. 50% polar organic solvent (e.g. ethanol): 50% $H_2O$). The extraction can be by cold percolation or by soxhlet.

In a further aspect of the invention there is provided use of an organic solvent extract of *Galega officinalis* comprising galegine and/or at least one polar organic solvent as a weight reducing agent in a mammal. In a preferred aspect of the invention the extract of Galega *officinalis* for use as a weight reducing agent in a mammal comprises a polar organic solvent and water. Preferably, the extract comprises a solvent system of 50% ethanol: 50% $H_2O$.

Galegine and related compounds can also be chemically synthesised. Generally, compounds of the invention may be synthesised according to procedures as outlined below.

For example, γ,γ- Dimethylallylamine can be synthesised according to the following procedure:

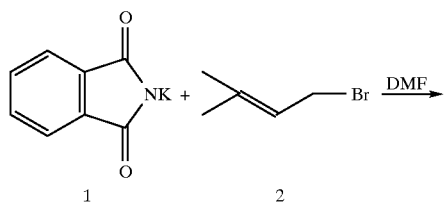

-continued

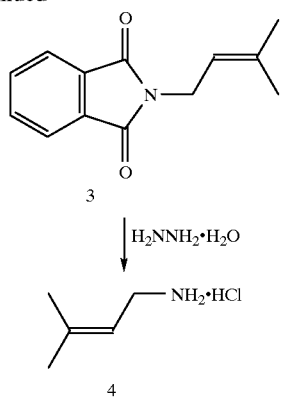

Amine 4 can be synthesised using the Gabriel synthesis of primary amines (ref. 2). Potassium phthalimide 1 can be treated with dimethyl allyl bromide 2 to form the N-alkylphthalimide 3. Subsequent treatment with hydrazine hydrate and hydrochloric acid can afford the target molecule 4.

Phenylmezhylguanidine hydrochloride can be synthesised according to the following procedure:

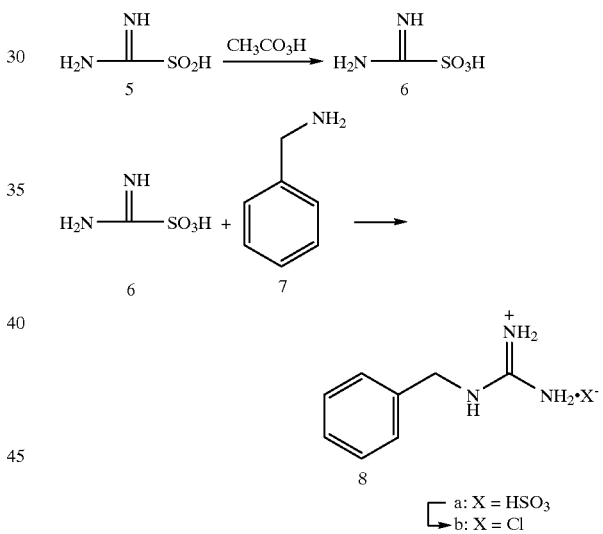

a: X = $HSO_3$
b: X = Cl

Aminoiminomethanesulfonic acid 6—synthesised from formamidinesulfonic acid 5 (ref. 3)—can undergo nucleophilic displacement of $HSO_3$—upon treatment with benzyl amine 7. The monosubstituted guanidine 8a can then be subsequently transformed to the solid hydrochloride salt 8b.

Allylguanidine sulphate may be synthesised according to the following outline:

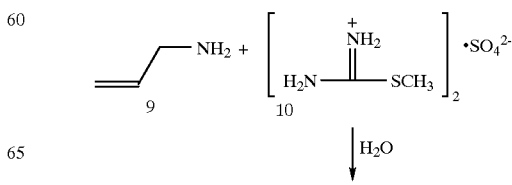

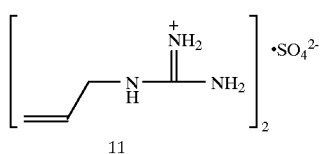

11

Target molecule 11 can be obtained via nucleophilic displacement of methane thiol from S-methyl isothiourea sulphate 10 by allyl amine (ref. 4).

γ,γ-Dimethylallylamidine hydrochloride may be synthesised as follows:

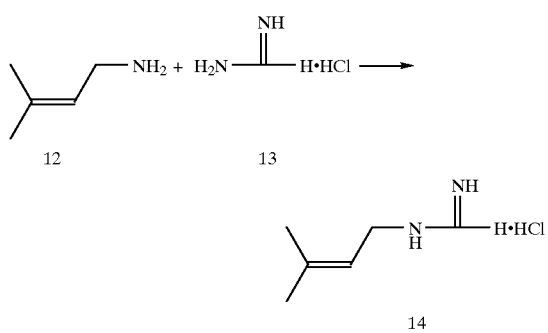

N-monoalkylated amidines are formed from N-unsubstituted amidines via a transamination reaction (ref. 5). Thus, reaction of formamidine hydrochloride 13 with γ,γ-dimethylallylamine 12 can afford the N-substituted amidine 14. The viscous oil is subsequently transformed to the picrate salt for structural analysis via conventional techniques.

References herein to weight reduction are to be construed to include either a reduction of the subject's actual weight after administration of a compound of formula (I), or a reduction in rate of weight gain in comparison to that of an untreated subject.

Subjects to be treated by the present invention include both human and animal (e.g. dog, cat, horse) subjects and are preferably mammalian subjects.

The weight reducing agent is administered in an amount effective to result in weight reduction. The weight reducing agent is preferably administered in a total amount per day of not more than 40 mg/kg body weight, more preferably not more than 20 mg/kg body weight and most preferably not more than 4 mg/kg. With respect to minimum dose, the weight reducing agent is preferably administered n a total amount per day of at least 0.02mg/kg, most preferably 3at least 0.2 mg/kg. The weight reducing agent may be administered once or several time a day.

The compounds of formula (I) and formula (II) may be administered per se or in the form of physiologically acceptable salts. Such physiologically acceptable salts include, but are not limited to, those prepared from the following acids: hydrochloric, hydrobromic, hydrochloric, sulphuric, nitric, phosphoric, maleic, acetic, salicylic, p-toluenesulphonic, tartaric, citric, isethionic, methanesulphonic and benzenesulphonic. Also, pharmaceutically acceptable salts, such as sodium, potassium, or calcium salts may be used. The compounds of formula (I) and/or formula (II) may be administered as pharmaceutical formulations, both for veterinary and for human medical use, which comprises at least one weight reducing agent together with one or more pharmaceutically acceptable carriers and optionally any other therapeutic ingredients. The carrier(s) must be pharmaceutically acceptable in the sense of being compatible with the other ingredients of the formulation and not unduly deleterious to the, recipient thereof.

The formulations include those suitable for oral, rectal or parenteral (including subcutaneous, intramuscular or intravenous) administration. Formulations for oral administration are preferred, particularly as solid or liquid food formulations.

The formulations may be prepared by any of the methods well known in the art. All methods include the step of bringing the compound of formula (I) and/or formula (II) into association with a carrier which constitutes one or more accessory ingredients. In general, :he formulations are prepared by uniformly and intimately bringing the active compound into association with a liquid carrier, a finely divided solid carrier, or both, and then, necessary, shaping the product into desired formulations.

Formulations of the present invention suitable for oral administraticn may be prepared as loose powder or granules; or in unit dosage forms as discrete units such as capsules, sachets, tablets or lozenges, each containing a predetermined amount of the weight reducing agent as a powder or granules; or a suspension in an aqueous liquor or non-aqueous liquid such as a syrup, an elixir, an emulsion or a draught.

A tablet may be made by compression or molding, optionally with one or more accessory ingredients. Compressed tablets may be prepared by compressing in a suitable machine, with the active compound being in a free-flowing form such as a powder or granules which is optionally mixed with a binder, disintegrant, lubricant, inert diluent, surface active agent or dispersing agent.

A syrup may be made by adding the active compound to a concentrated aqueous solution of a sugar, for example sucrose to which may also be added any accessory ingredient(s). Such accessory ingredient(s) may include flavourings, suitable preservatives an agent to retard crystallisation of the sugar, and an agent to increase the solubility of an other ingredient, such as a polyhydric alcohol, for example glycerol or sorbitol.

Formulations for parenteral administration conveniently comprise a sterile aqueous preparation of the active compound, which is preferably isotonic with the blood of the recipient.

Formulations for rectal administration may be presented as suppository with a suitable carrier such as cocoa butter, or hydrogenated fats or hydrogenated fatty carboxylic acids.

In addition to the aforementioned ingredients, the formulations of this invention may further include one or more accessory ingredient(s) selected from diluents, buffers, flavouring agents, binders, disintegrants, surface active agents, thickeners, lubricants, preservatives (including antioxidants) and the like.

FIG. 1 Effect of different dietary concentrations of galegine on various parameters in normal mice. 1a: Daily body weight (each point is mean ±SEM of 7 observations). Effect of treatment * P<0.05, ** P<0.01, two-way ANOVA for repeated measures. 1b: Daily food intake. (1b:each value is the mean per mouse for each cage).

Figure 2:
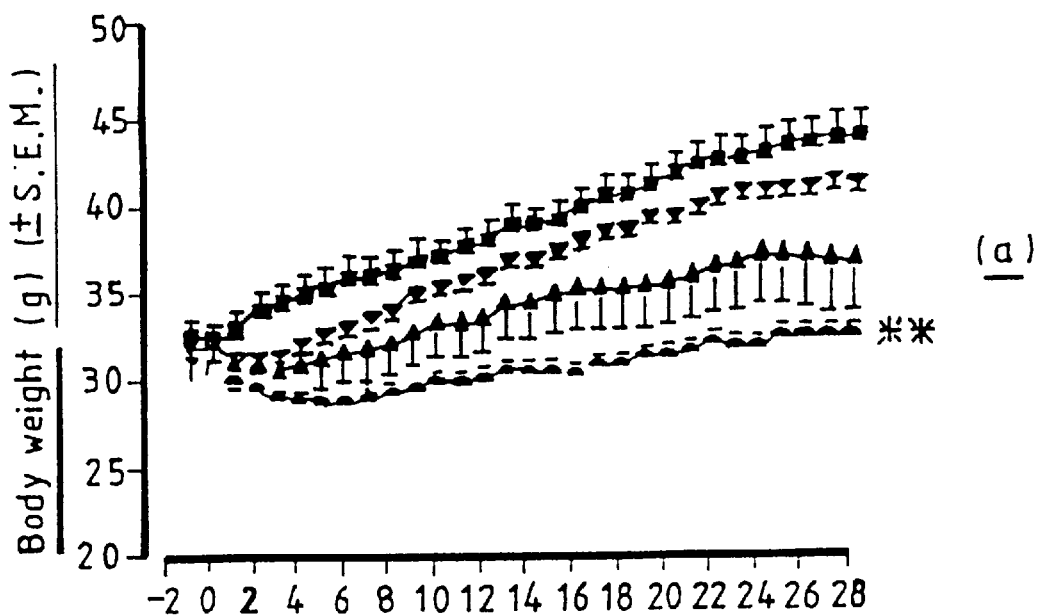
Figure 2:
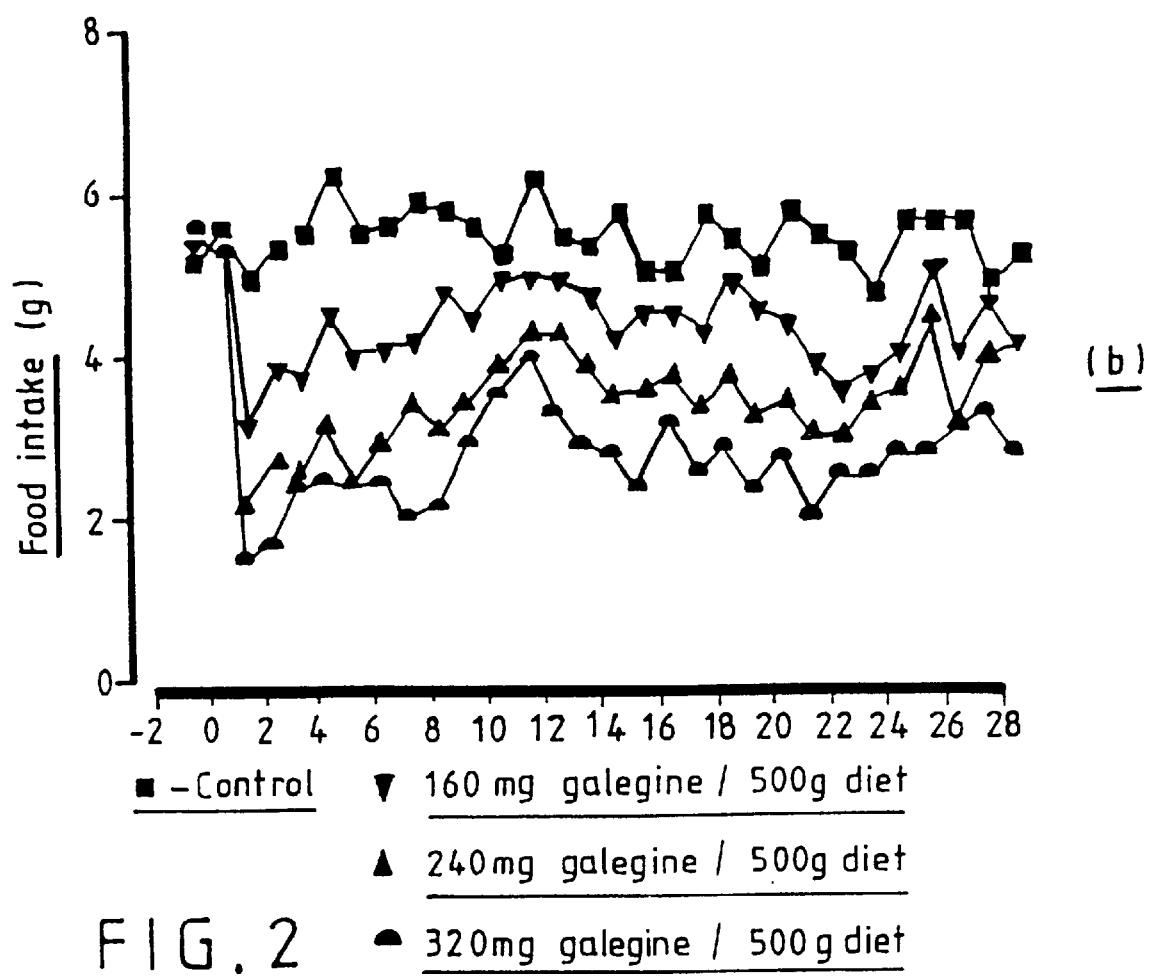

FIG. 2 Effect of different dietary concentrations of galegine on a various parameters in genetically obese (ob/ob) mice. 2a: Daily body weight (each point is mean USEM of 7 observations). Effect of treatment ** P<0.01, two-way ANOVA for repeated measures. 2b: Daily food (2b: each value is the mean per mouse for each cage).

Figure 3:
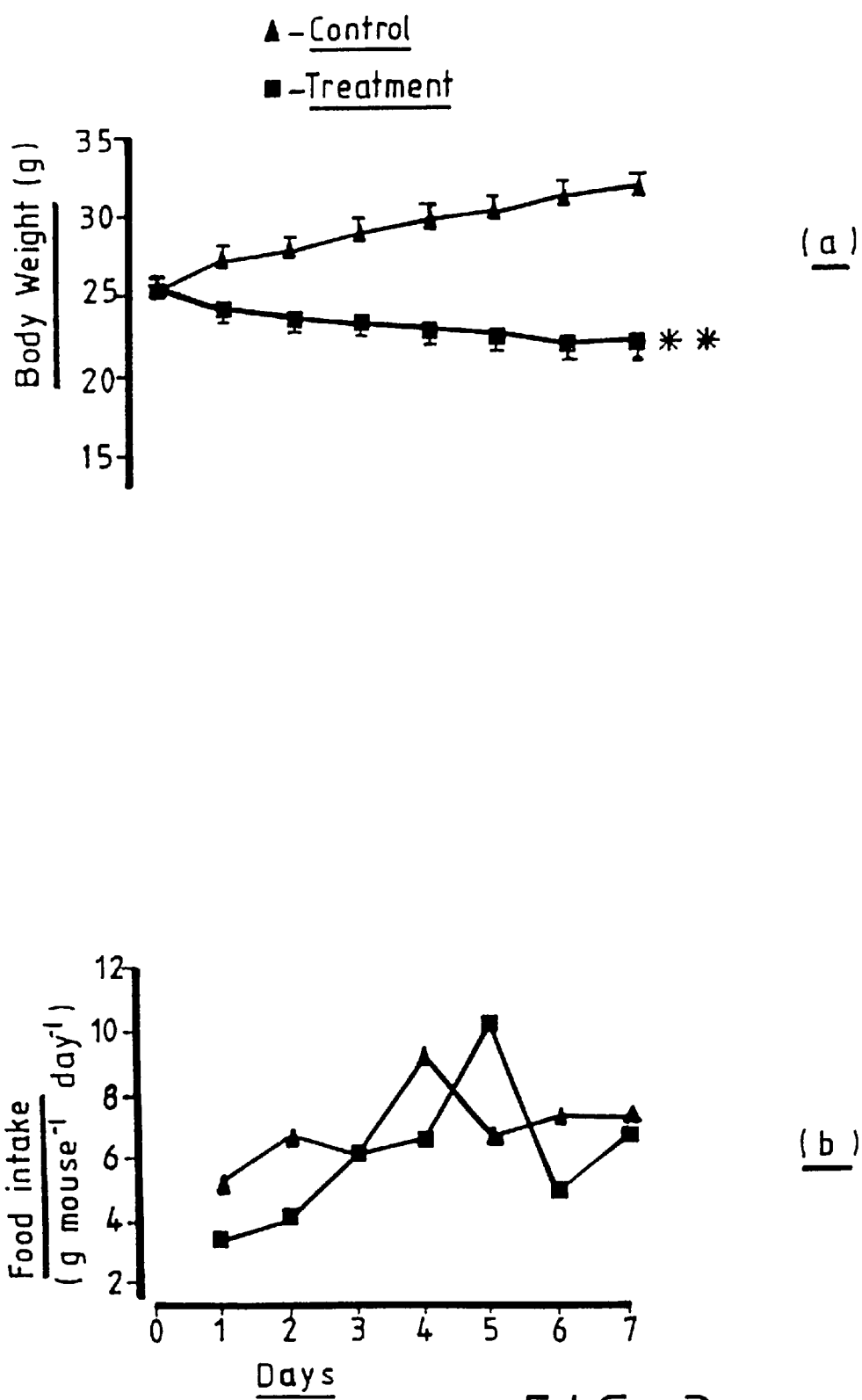

FIG. 3 Effect of the 50%-ethanol-water cold extract or *galega officinalis* on various parameters in normal mice. 1a: Daily body weight each point is mean ±SEM of 7–8 observations). Effect of treatment  P<0.01, two-way ANOVA for repeated measures. 3b: Daily food in-take.  P<0.01 compared to control, Student's unpaired t-test.

Figure 4:
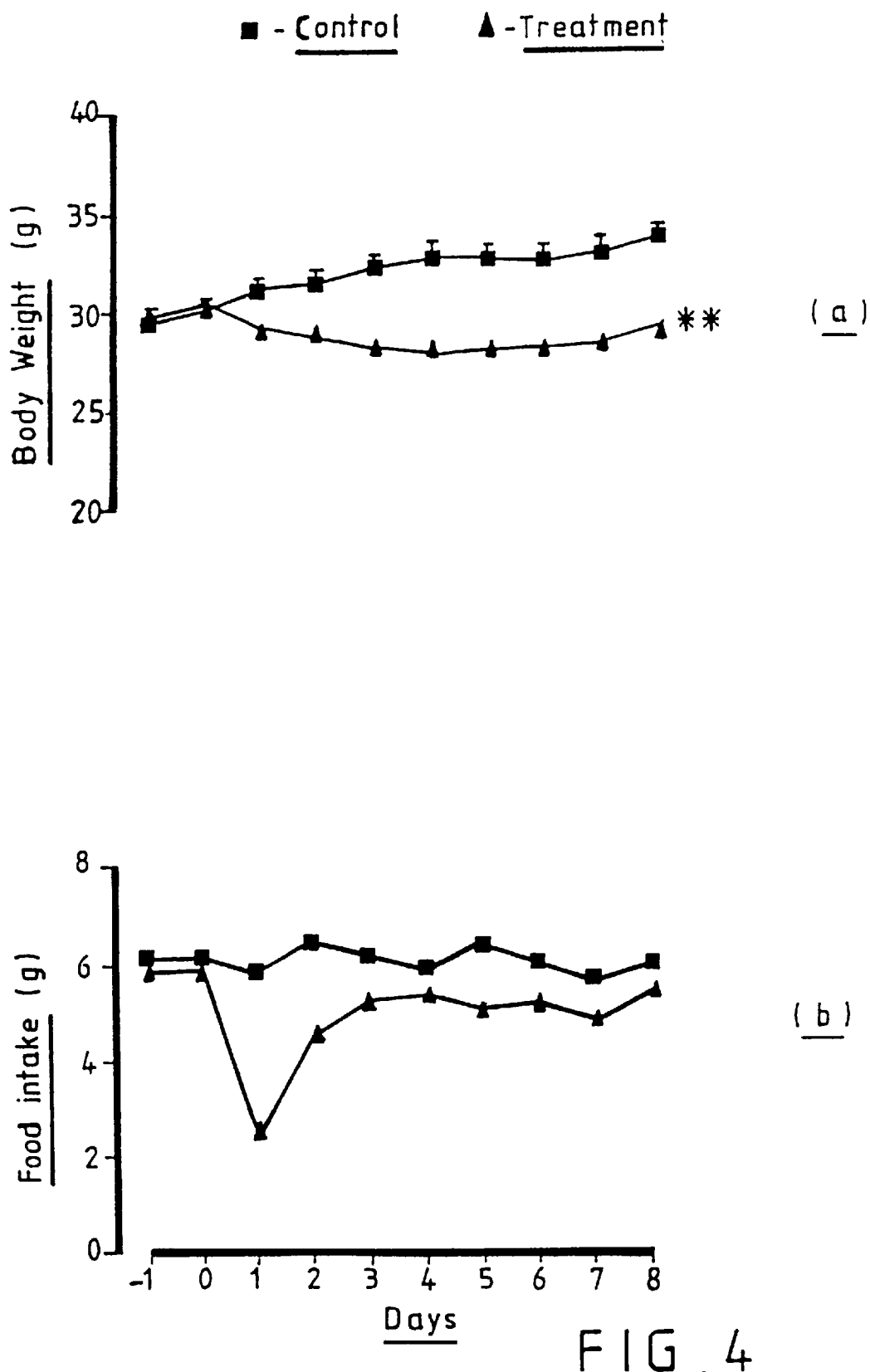

FIG. 4 Effect of the 50%-ethanol - water soxhlet extract of *Galega officinalis* on various parameters in normal mice (8 day study). 4a: Daily body weight (each point is mean ±SEM of 7–8 observations). Effect of treatment  P<0.01, two-way ANOVA for repeated measures. 4b: Daily food intake.  P<0.01, Student's unpaired t-test.

Figure 5:
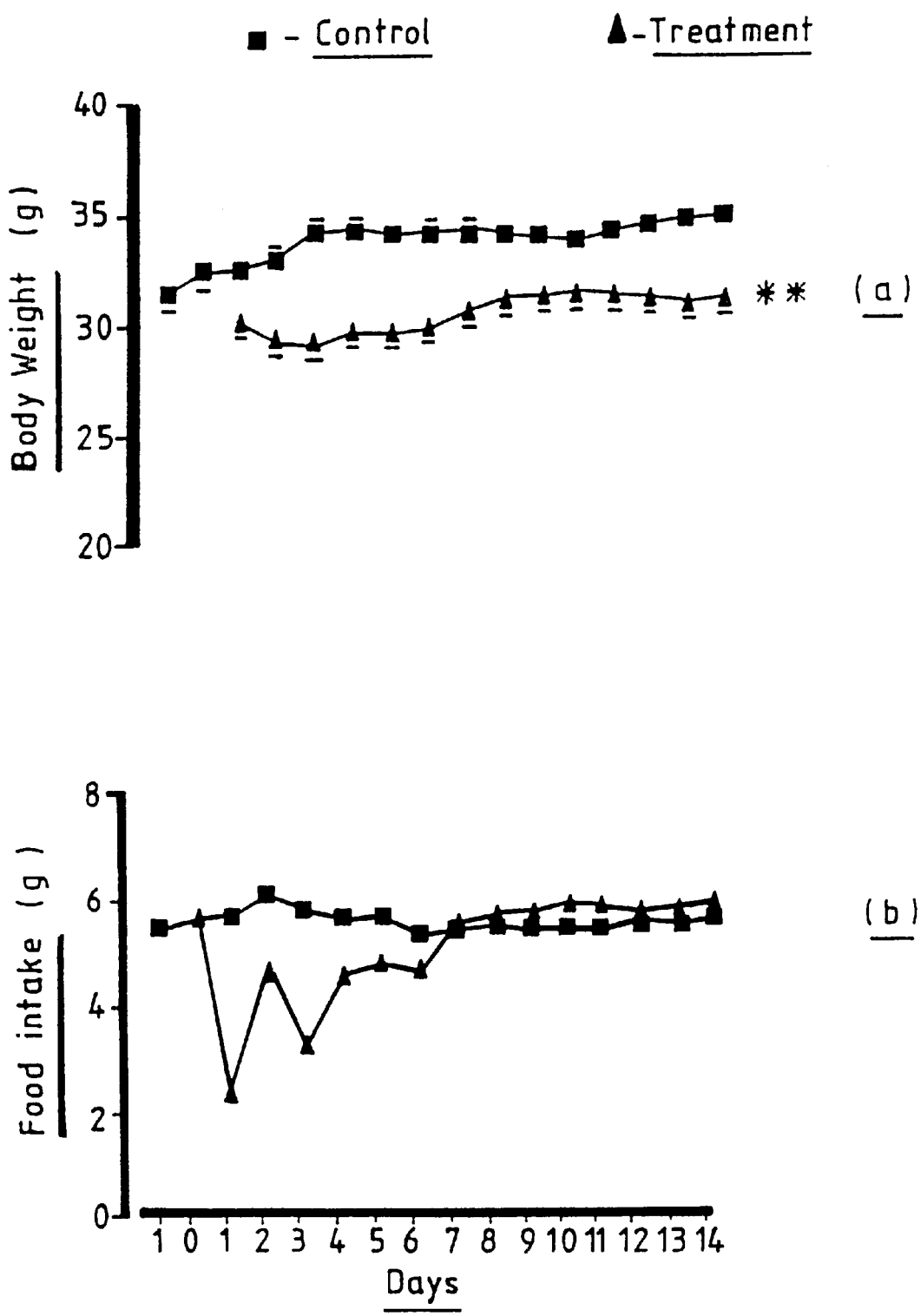

FIG. 5 Effect of the 50%-ethanol - water soxhlet extract of *Galega officinalis* on various parameters in normal mice (14 day study). 5a: Daily body weight (each point is mean ±SEM of 7 observations). Effect of treatment  P<0.01, two-way ANOVA for repeated measures. 5b: Daily food intake.  P<0.01, Student's unpaired t-test.

Figure 6:
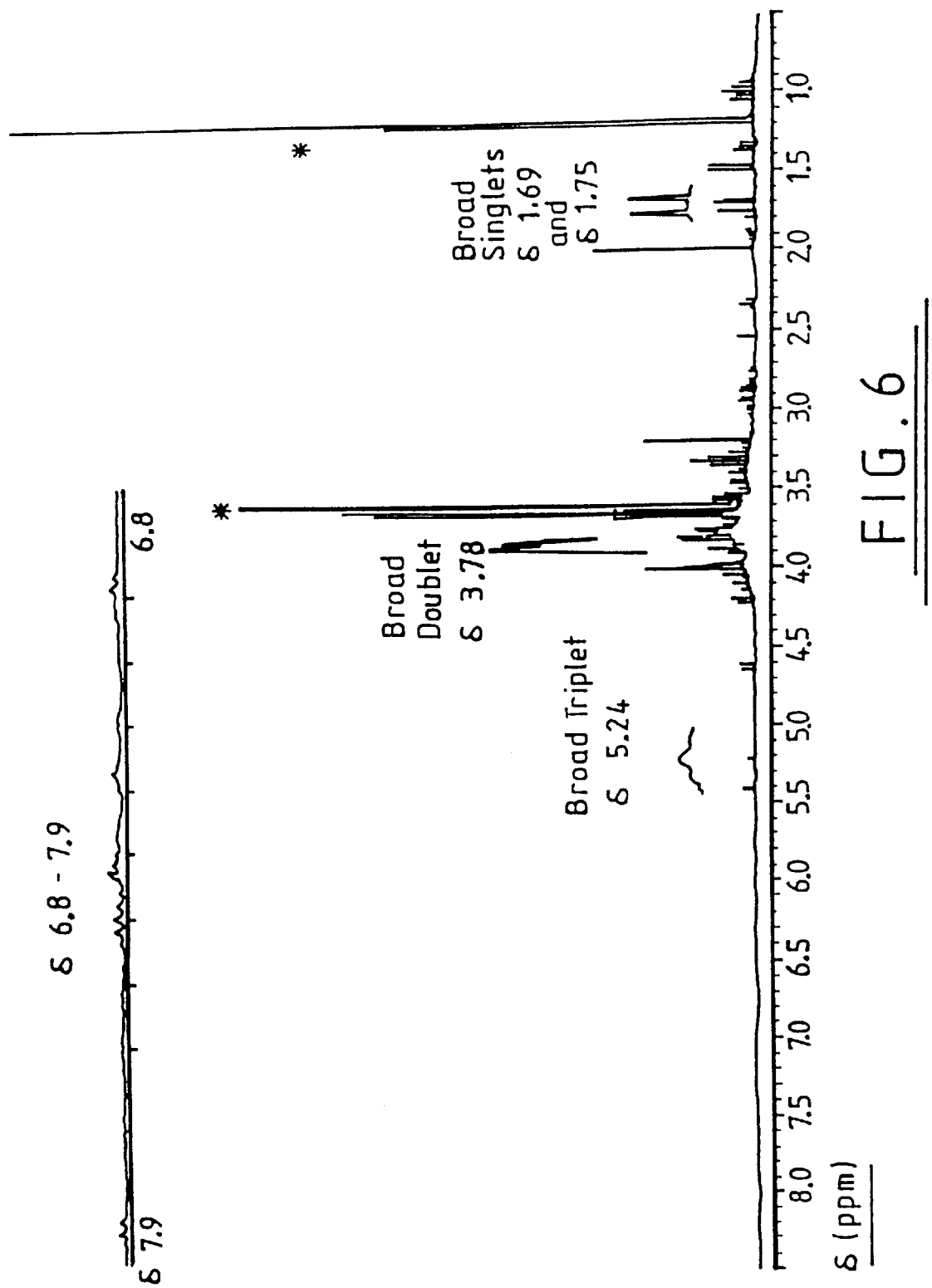

FIG. 6 400.14 MHz proton NMR, water supressed spectrum of the ethanol-water extract of *Galega officinalis*. Residual ethanol signals *. Examples 1, 4 and 6 to 8 inclusive illustrate further compounds of Formula (1).

Examples 4 and 6 to 8 inclusive illustrate further compounds of Formula (1).

EXAMPLE 1

Weight Reducing Effect of Galegine on Normal Mice

Galegine was synthesised by and obtained from Aston Molecules Limited.

This example shows that when galegine is administered to mice, as part of their feed, the mice do not gain weight to the same extent as untreated mice.

This experiment consists of four treatments, as follows:

(1) 160 mg of galegine was added to 500 g of mice feed;
(2) 240 mg of galegine was added to 500 g of mice feed;
(3) 320 mg of galegine was added to 500 g of mice feed;
(4) a negative control group to which no galegine was added.

The procedure for this experiment is as follows. Each group of mice (7 mice per group) were allowed to feed and drink freely. The experiment was carried out for 14 days. Body weight and intakes of food were measured daily.

The results of the experiment are shown in FIG. 1. It can be seen that all treated groups, showed a sharp drop in food intake on Day 1. All groups then showed a gradual return towards the control Level, with the 160 and 240 mg/500 g groups showing a transient increase in food intake above the control level.

Mean body weight in all treated groups was found to be lower than that of the untreated control group. The 320 mg/500 g group showed the greatest reduction in weight gain over the 14 day period.

The mice did not display overt symptoms or steatorrhoea and symptoms of diarrhoea were not observed.

EXAMPLE 2

Weight Reducing Effect of Galegine on Genetically Obese (ob/ob) Mice

This experiment was carried out in the manner described in Example 1 with the exception that the mice to be treated were genetically obese (ob/ob) mouse strain, and data was collected for 28 days.

The results of this experiment are shown in FIG. 2. It can be seen that all treated groups showed a sharp drop in food intake on Day 1. Food intake remained below the levels of the control group for the duration of the experiment.

Mean body weight in all treated groups was found to be lower than that of the untreated control group. The 320 mg/500 g group showed the greatest reduction in weight gain over the 28 day period. The mice did not display overt symptoms of steatorrhoea and no symptoms of diarrhoea were observed.

As in Example 1 no overt symptoms of steatorrhoea and symptoms of diarrhoea were not observed.

EXAMPLE 3

N-(γ,γ-Dimethylallyl-Phthalimide

A mixture of 4-bromo-2-methyl-2-butene (Aldrich) (5.51 g; 37 mmol), potassium phthalimide (Aldrich) (7.41 g; 40 mmol) and dimethylformamide (40 cm$^3$) was heated at 115° C. for 1.5 h. Dichloromethane and water were added to the cooled reaction mixture and extracted with 3×15 cm$^3$ portions of chloroform. The combined organic extracts were washed with 0.2 N sodium hydroxide (20 cm$^3$) and water (20 cm$^3$), :hen dried (Na$_2$SO$_3$), filtered and concentrated in vacuo, to afford a colourless crystalline solid (6.55 g; 82%). An analytically pure sample was obtained following recrystallisation from absolute alcohol, m.p. 99–101° C. (Lit$^6$. 100° C.).

Found : C, 72.32; H, 6.02; N, 6.44%
Calc. for C$_{13}$H$_{13}$NO$_2$: C, 72.54; H, 6.09; N, 6.51%
vmax (KBr)/cm$^4$: 3185, 3172, 3107, 3068, 3025 (Ar-Hstr), 2960, 2904, 2829, 2789, 2613, 2588 (Al,Hstr), 1589, 1562, 1547, 1475 (C═Cstr & C═Ostr).
δH (250 MHZ, CDCl$_3$) 1.70 (3H, s, CH$_3$), 1.83 (3H, S, CH$_3$), 4.25 (2H, d, J72 Hz, CH$_2$—), 5.26 (1H, m, vinyl C—H), 7.67–7.72 (2H, m, aryl C—H), 7.78–7.84 (2H, m, aryl C—H).

EXAMPLE 4

γ,γ-Dimethylallylamine

A mixture of N-(γ,γ-dimethylallyl)-phthalimide (Example 3) (3.0 g; 13.9 mmol), ethanol (10cm$^3$) and 85% hydrazine hydrate (0.89 g; 15.2 mmol), was heated under reflux for 2 h, cooled, then treated with 10 M hydrochloric acid (1.52 cm$^3$; 15.2 mmol) and filtered. The collected phthalhydrazide was triturated with water, filtered and the combined filtrates concentrated in vacuo. The residue was treated with a solution of 85% potassium hydroxide (1.1 g; 16.4 mmol) in water (5 cm$^3$) and extracted with diethylether. The combined extracts were dried over potassium hydroxide and distilled through a fractionating column. The fractions collected between m.p. 96–98° C. were treated with hydrochloric acid etherate to afford a colourless powder (0.90 g; 53%) , m.p. 200–201° C. (Lit$^6$ m.p. 201° C.)

Found : C, 48.92; H, 10.10; N, 11.24%. MH$^+$, 124.0572, 122.0650
Calc. for C$_5$H$_{12}$NCl : C, 49.38; H, 9.95; N, 11.52%. M, 123.0629, 121.0658
vmax (KBr)/cm$^{-1}$: 3200–2890 (N-Hstr), 2777, 2690, 2615, 2562 (Al-Hstr), 1681 (N-Hdef), 1597 (C═Cstr).
δH [250 MHz, (CD$_3$),SO] 1.64 (3H, s, CH$_3$), 1.70 (3H, s, CH$_3$), 3.34 (2H, d, J7.2 Hz CH$_2$), 5.23 (1H, br at, vinyl C—H), 8.21 (3H, br s, exch, NH$_3$).

EXAMPLE 5

Aminoiminomethanesulfonic Acid

To a stirring suspension of formamidinesulfonic acid (Aldrich) (3.24 g; 30 mmol) in acetic acid (10 cm$^3$), in an ice-bath, peracetic acid (CAUTION, 36–40% in acetic acid, 7.5 cm$^3$, 39 mmol) was added dropwise at such a rate that the temperature was maintained below 20° C. After addition was complete, the mixture was stirred at room temperature for 16 h. During reaction the fine white suspension was replaced by larger crystals of product, which were removed by filtration and washed with absolute alcohol to give (3.46 g, 93%) colourless crystals, m.p. 121–122° C. (dec). The product was used in subsequent reactions without further purification.

EXAMPLE 6

Phenylmethylauanidine Hydrochloride

Equimolar amounts of benzyl amine (Aldrich) (1.07 g; 10 mmol) and a suspension of aminoiminomethanesulfonic acid (Example 5) (1.24 g; 10 mmol) were stirred in absolute methanol (5 cm$^3$) at room temperature until the mixture became clear (5 min) and then stirred for a further 3 h. The solvent was removed under reduced pressure to afford a viscous residue. Subsequent trituration with diethylether— to remove unreacted benzyl amine—was followed by addition of dichloromethane and cold 2 M sodium hydroxide. The dichloromethane layer was dried (Na$_2$SO$_4$), then concentrated in vacuo. HCl etherate was added to the colourless oil to produce a colourless solid (0.647 g; 35%), m.p. 169–171° C.
Found C, .51.49; H, 6.59; N, 22.48%. M$^+$—Cl, 150.1092.

Calc. for C$_4$H$_{12}$N$_3$Cl : C, 51.76; H, 6.51; N, 22.63%. M, 187.0690, 185.0720.

δH [250 MHz, (CO$_3$)$_2$SO] 4.40 (2H. d, J6.2 Hz, PhCH$_2$—), 7.1–7.8 (9H, m & [br s], exch., N—H and aryl C—H), 3.29 (1H, m, aryl C—H).
vmax (KBr)/cm$^3$: 3400–3000 N—H str and Ar—H str), 2981, 2939, 2924, 2878, 2848, 2761. 2696 Al—H str) , 1971, 1955, 1894, 1878, 1834, 1817 (C=N str), 1684–1610, 1567 (N—H def and C=C str).

EXAMPLE 7

Allyicuanidine Sulphate

Allylamine (Aldrich) (2.85 g; 0.05 mmol) and 2-methyl-2-thiopseudourea sulphate (Sigma Chemical Co.) (5.22 g; 37.5 mmol) in water (30 cm$^3$), were heated under reflux for 2.5 h, under nitrogen. The colourless solution was evaporated to dryness in vacuo to yield colourless crystalline material. Recrystallisation from ethanol/water (2:1) afforded crystalline needles (3.71 g; 67%), m.p. 208–210° C.
Found : C, 32.43; H, 6.96; N. 28.44; S, 10.92%. MHZ, 297.1362.
Calc. for C$_3$H$_{20}$N$_6$O$_4$S : C, 32.42; H, 6.80; N, 28.36; S, 10.82%. M, 296.1267.
δH (250 MHz, CF$_3$C$_2$H) 3.77 (4H, M, CH$_2$), 5.26 (4H, M, vinyl C—H), 5.74 (2H, M, vinyl C—H).
vmax (KBr)/cm$^3$450–3100 (N—H str), 3083, 3016 (vinyl C—H str), 2983, 2935, 2877, 2831, 2723(Al—H str) , 2084, 1967, 1863 (C=N str), 1670–1550 (N—H a C=C str).

EXAMPLE 8

γ,γ-Dimerhylallyiamidine Hydrochloride

Formamidine hydrochloride (Aldrich) (0.57 g; 7.05 mmol) was suspended in absolute alcohol (8 cm$^3$) and nitrogen introduced above the liquid. γ,γ-Dimethylallyl amine 0.6 g; 7.0 mmol) was added and the reaction mixture stirred for 20 minutes at room temperature, then heated under reflux for 2 hours. After cooling, the ethanol was removed under reduced pressure and the residue triturated with diethyl ether to remove any unreacted γ,γ-dimethylallylamine. The residue was concentrated in vacuo to produce a yellow-orange viscous oil. A small quantity of the crude product was taken up in water and treated with hot aqueous picric acid. The resulting picrate salt was used to identify the amidine's structure.

1. Hydrochloride Salt

δH [250 MHz, (CD$_3$)$_2$SO] 1.64 (3H, S, CH$_3$), 1.69 (3H, S, CH$_3$), 3.87 (2H, d, J6.95 Hz, CH$_2$), 5.25 (1H, M, vinyl C—H), 7.75–8.10 (1H, m, amidine C—H 9.0–9.7 (2H, br m, N—H), 9.95 (1H, br s, N—H).
vmax (LF)/cm$^3$: 3400–2800 (N—H str & C—H str), 1947 (C=N str), 1705, 1633, 1537 (N—H def & C=C str).

2. Picrate Salt

Found : C, 42.46; H, 4.42; N, 19.88%.
C$_{12}$H$_{15}$N$_5$O, requires : C, 42.23; H, 4.43; N, 20.52%.
δH [250 MHz, CD$_3$)$_2$SO] 1.65 (3H S, CH$_3$) 1.71(3H, S, CH$_3$) 3.8–3.95 (2M, CH$_2$) 5.18 (1H, vinyl C—H), 7.92 (1H, m, vinyl C—H), 8.4–9.3 (3H, br m, excn, N—H) 3.59 (2H, s, aryl C—H).
vmax (KBr)/cm$^3$: 3401, 3213 N—H str), 3129, 3099, 3089, 3060 (vinyl C—H str) , 2971, 2941, 2919 (Al—H str), 1708, 1670, 1643, 1604, 1560 (C=C str & N—H der).

References

1. D. Semenow, C-H. Shih and W. G. Young, J. Am. Chem. Soc., 1958, 80, 5472–5.
2. J. D. Roberts, R. H. Mazur, J. Am. Chem. Cos, 1951, 73, 2509–23.
3. K. Kim, Y-At. Lin and S. Mosher, Tetrahedron Lett., 1988, 29, 3183–3186.
4. C. E. Braun, J. Am. Chem. Soc., 1933, 56, 1280–84.
5. P. Reynauld, J-D. Brion and G. Menard, Bull. Soc. Chem. Fr., 1978, II-449–56.
6. G. Desvages and M. Olomucki, Bull. Soc. Chem. Fr., 1969, 9, 3229–32.

EXAMPLE 9

Preparation of Extracts of Galega

A number of extracts of galega were incorporated into the diet in an amount eauivalent to 10% w/w of the dried plant material in the diet. Thus, 50 g of powdered galega was extracted to exhaustion, first with ethyl acetate followed by 50% ethanol- water, extraction was by cola percolation or by soxhlet, using methods known in the art. Groups of normal mice received extract-containing diet or control diet for periods of 7–14 days.

Preparation of Diet Containing Galegine

Diets containing galegine at concentrations of 160, 240, 320, and 640 mg per 500 g, or control diet were administered to groups of normal or genetically obese (ob/ob) mice for periods of 7–28 days.

Measurements

In all studies, body weight and intakes of food and water were measured on a daily basis. At the end of the treatment period serum glucose and insulin levels were determined.

Spectroscopic and Chromatoaraphic Analysis of 50% Ethanol-Water Extracts

400 MHz H NMR and $^1$H-$^1$H-cosy 45 were performed on the cold ethanol-water extract. Thin layer chromatography (TLC-silica-gel) was performed on cold and soxhlet ethanol-water extracts. The solvent system used was chloroform (6.5)-methanol (3.5)—water (1.0). The plate was developed with Sakaguchi reaaent which gives a reddish-orange colour with galegine.

Results

Studies with Extracts of Galega

The cold and soxhlet 50%-ethanol-water extracts contained compound(s) which caused significant and sustained weight loss (P<0.01) (FIGS. 3, 4 and 5). Food intake was initially depressed (FIGS. 3a, 4b and 5b) but returned to the control level within 3–7 days.

As in Examples 1 and 2 overt symptoms or steatorrhoea and symptoms of diarrhoea were not observed.

The $^1$H NMR spectrum of the 50%-ethanol-water cold extract (FIG. 6) showed the presence of glycose (sugar)-type compounds (c.a. δ3.5–5.0), aromatic-type compounds (δ6.8–8.0) as well as galegine (c.a. δ5.24, 3.78, 1.68 and 1.75).

TLC was performed with the 50%-ethanol-water extracts and with pure galegine. On development of the plate, the extracts produced reddish-orange spots with very similar Rf values to that of pure galegine (approximately 0.7).

We claim:

1. A method of attaining weight reduction in a mammal which comprises administering to the mammal an effective, non-toxic amount of a compound of formula (I)

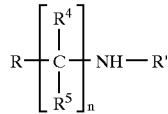
(I)

wherein
R is selected from the group phenyl and

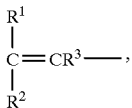

where
R$^1$, R$^2$ and R$^3$ are independently selected from the group H, C$_{1-6}$ alkyl, C$_{2-6}$ alkenyl, and C$_{2-6}$ alkynyl;
R$^4$ and R6 are independently selected from H, C$_{1-6}$ alkyl, C$_{2-6}$ alkenyl, and C$_{2-6}$ alkynyl,
R' is

wherein R$^6$ is selected from the group H, NH$_2$ and C$_{1-6}$ alkyl; n is a whole integer from O to 6; with the proviso that when R' is

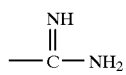

and n=0, R is not phenyl and when R' is

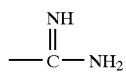

and n is 1, 2, 3 or 4 and R$^4$ and R$^5$ are both H, R is not phenyl and the compound is not galegine; or a physiologically acceptable salt thereof.

2. The method according to claim 1 wherein:
R$^1$ and R$^2$ are independently selected from H and C$_{1-6}$ alkyl;
R$^3$ is selected from H or C$_{1-6}$ alkyl;
R$^4$ and R$^5$ are independently selected from H or C$_{1-6}$ alkyl;
n is 1 or 2.

* * * * *

UNITED STATES PATENT AND TRADEMARK OFFICE
CERTIFICATE OF CORRECTION

PATENT NO. : 5,945,455

DATED : August 31, 1999

INVENTOR(S) : Palit et al.

It is certified that error appears in the above-identified patent and that said Letters Patent is hereby corrected as shown below:

Title page, [56] References Cited, FOREIGN PATENT DOCUMENTS, line 2, "94/03714" should read --93/03714--.

Title page, [56] References Cited, FOREIGN PATENT DOCUMENTS, insert the following: --330 629   8/1989   EPO--.

Title page, [56] References Cited, OTHER PUBLICATIONS, line 8, "Indulinähnliche" should read --Insulinähnliche--; line 9, "Arginylverbinsungen" should read --Arginylverbindungen--.

Column 2, lines 58-59, cancel "BRIEF DESCRIPTION OF THE DRAWINGS".

Column 6, after line 57, insert the following: --BRIEF DESCRIPTION OF THE DRAWINGS--.

Column 12, line 6, after "$C=CR^3$—" cancel the comma (,); line 13, "R6" should read --$R^5$--; line 22, "O to 6" should read --0 to 6--.

Signed and Sealed this

Fourteenth Day of March, 2000

*Attest:*

Q. TODD DICKINSON

*Attesting Officer*       *Commissioner of Patents and Trademarks*